United States Patent
Hiss, III (10) Patent No.: US 6,439,027 B1
(45) Date of Patent: Aug. 27, 2002

(54) PARTICULATE MASS MEASUREMENT APPARATUS WITH REAL-TIME MOISTURE MONITOR

(75) Inventor: John Hiss, III, Castleton, NY (US)

(73) Assignee: Rupprecht & Patashnick Company, Inc., Albany, NY (US)

( * ) Notice: Subject to any disclaimer, the term of this patent is extended or adjusted under 35 U.S.C. 154(b) by 17 days.

(21) Appl. No.: 09/636,147

(22) Filed: Aug. 10, 2000

(51) Int. Cl.[7] .................. G01F 1/70; G01N 15/02; G01N 15/06; F26B 21/06; B01D 37/00
(52) U.S. Cl. ............ 73/28.01; 73/863.22; 73/863.23; 73/31.07; 422/88
(58) Field of Search ............ 73/28.01, 24.03, 73/23.33, 31.07, 863.23, 863.22, 863.52; 422/83, 88, 865.5, 28.05, 28.03

(56) References Cited

U.S. PATENT DOCUMENTS

| | | | | |
|---|---|---|---|---|
| 3,727,048 A | * | 4/1973 | Haas | 250/43.5 MR |
| 3,784,902 A | * | 1/1974 | Huber | 324/32 |
| 3,920,422 A | * | 11/1975 | Pircon | 55/90 |
| 4,507,875 A | | 4/1985 | Hirsh | 34/44 |
| 5,006,227 A | * | 4/1991 | Belm et al. | 209/143 |
| 5,090,233 A | * | 2/1992 | Kogure et al. | 73/28.05 |
| 5,332,512 A | * | 7/1994 | Wells | 210/790 |
| 5,369,981 A | * | 12/1994 | Mery | 73/28.01 |
| 5,567,865 A | * | 10/1996 | Hauf | 73/28.01 |
| 5,571,946 A | | 11/1996 | Koshi et al. | 73/28.01 |
| 5,665,902 A | * | 9/1997 | Wang, II et al. | 73/28.01 |
| 5,672,827 A | * | 9/1997 | Jursich | 73/861.07 |
| 5,739,413 A | * | 4/1998 | Kohn et al. | 73/23.31 |
| 5,792,966 A | | 8/1998 | Weitz et al. | 73/861.61 |
| H1757 H | | 11/1998 | Seltzer | 73/863 |
| 5,932,795 A | * | 8/1999 | Koutrakis et al. | 73/28.01 |
| 5,970,781 A | | 10/1999 | Hiss, III et al. | 73/28.01 |
| 6,016,688 A | | 1/2000 | Hiss, III et al. | 73/28.01 |
| 6,106,592 A | * | 8/2000 | Paranjpe et al. | 95/65 |

OTHER PUBLICATIONS

Patent Abstracts of Japan, vol. 1998, No. 08, Jun. 30, 1998 & JP 10 062404 A (Nippon Steel Corp.), Mar. 6, 1998, abstract; figure 1.

* cited by examiner

Primary Examiner—Hezron Williams
Assistant Examiner—David J. Wiggins
(74) Attorney, Agent, or Firm—Heslin Rothenberg Farley & Mesiti P.C.

(57) ABSTRACT

The mass of particulate of an effluent gas flowing in a stack is measured with a mass measurement assembly in which sampling is isokinetically controlled by determining in real-time the molecular weight of the effluent gas, and in particular, determining the moisture content of water vapor in the effluent gas. Readings from a pair of flow sensors connected in series and separated by a dryer are compared to provide a real-time moisture measurement of the effluent gas. The moisture measurement is used to determine a total molecular weight of the effluent gas in real-time and the velocity of the effluent gas in real-time for isokinetic sampling during measurement of the mass of particulate flowing in the effluent gas.

24 Claims, 2 Drawing Sheets

PARTICULATE MASS MEASUREMENT APPARATUS WITH REAL-TIME MOISTURE MONITOR

TECHNICAL FIELD

The present invention relates generally to gas moisture measurement, and more particularly, to particulate mass measurement instruments operable to measure the moisture content of effluent gas in real-time for real-time adjustment of isokinetic sampling during measurement of the mass of particulate matter flowing in a stack or other exhaust conduit.

BACKGROUND OF THE INVENTION

Particulate mass measurement of effluent gas flowing in a stack or other exhaust conduit of such stationary sources as coal burning facilities, garbage incinerators, hazardous waste type incinerators, concrete plants, paper/pulp processing plants and the like, is important because of the relationship between particulate matter and adverse health effects. Various regulatory agencies around the world require the continuous mass measurement of particulate matter from stacks.

Obtaining a representative sample of the effluent gas flowing in the stack for particulate mass measurement generally requires that the sample be obtained isokinetically. An isokinetic sample is obtained by maintaining the kinetic energy of the sample as it enters a sampling nozzle of a particulate mass measurement instrument. Kinetic energy is a function of the mass and velocity of the sample. Since the mass of the sample is generally constant, the kinetic energy of the sample may be maintained by matching the velocity of the effluent gas flowing in the stack with the velocity of the sample of the effluent gas flowing through the nozzle. That is to say, an isokinetic sample is one that is drawn with a velocity equal to the velocity of the effluent gas in the stack.

The velocity, V, of the effluent gas flowing in the stack is typically determined using a pitot tube disposed in the effluent gas flowing in the stack according to the following relationship:

$$V = C \times (PitotDP)^{0.5} \times (T/(P \times Ms))^{0.5} \quad (1)$$

where:

C is the pitot tube calibration constant;

PitotDP is the measured pressure drop across the pitot tube;

T is the absolute effluent gas temperature;

P is the absolute pressure of the effluent gas; and

Ms is the molecular weight of the effluent gas including water vapor.

Typically, the temperature, T, is determined using a temperature sensor or thermocouple, the pressure drop across the pitot tube, PitotDP, is determined using pressure transducers, and the absolute pressure, P, is determined using a pressure transducer.

While the above-noted determinations of temperature and pressures may be made in real-time, the molecular weight of the effluent gas including water vapor, Ms, is user supplied and estimated which results in an approximation of the velocity, V, of the effluent gas flowing in the stack. In particular, the molecular weight of the effluent gas, Ms, is based on the dry molecular weight of the gas (e.g., obtained using carbon dioxide ($CO_2$) and oxygen ($O_2$) sensors, with the remainder of the gas composition assumed to be nitrogen ($N_2$) and guessing at the moisture content, i.e., proportion of water vapor, by volume, in the effluent gas flowing in the stack.

During the sampling, the moisture content of the water vapor is determined, for example, according to U.S. Environmental Protection Agency (EPA) Method 4. In EPA Method 4, a known volume of effluent gas is removed from the effluent gas stream via condensation in a series of chilled impingers and absorption in silica gel. The mass of water collected is then measured and related back to the known volume of the effluent gas to determine the moisture content of the gas stream. Drawbacks with such a method include the moisture content being an average over time and the average moisture content being determined only following the completion of the sampling. The goal is to maintain agreement between the estimated velocity of the effluent gas flowing in the stack and the velocity of the effluent gas (i.e., using the measured average moisture content) within +/−10 percent which is considered satisfactory for achieving isokinetic conditions.

There is a need for an apparatus and method for measurement of the moisture content in an effluent gas in real-time for real-time adjustment of the isokinetic sampling of the effluent gas during particulate mass measurement. More generally, such moisture measurements are needed for determining mass flow and total volumetric flow rate of an emission source in order to calculate the mass emission rate of regulated pollutants. Continuous or real-time moisture measurements are desired because many pollutants are measured on a continuous basis by continuous emission monitors (CEMs).

SUMMARY OF THE INVENTION

The present invention provides, in a first aspect, a particulate mass measurement apparatus for measuring mass of particulate of effluent gas flowing in a stack. The apparatus includes a mass measurement assembly for measuring the mass of particulate of the effluent gas flowing in the stack, means for measuring in real-time moisture content of the effluent gas flowing in the stack, and a controller for controlling isokinetic sampling of the effluent gas measurable by the mass measurement assembly based on real-time moisture content of the effluent gas flowing in the stack.

In another aspect, a method for measuring mass of particulate of effluent gas flowing in a stack includes determining a moisture content measurement of the effluent gas in real-time, obtaining an isokinetic sample of a portion of the effluent gas based on the real-time moisture content measurement of the effluent gas, and obtaining a mass of particulate measurement of the isokinetic sample.

In a third aspect, a moisture measurement monitor, includes a first flow sensor for determining a flow rate of a portion of gas having water, a dryer for removing the water from the portion of gas, a second flow sensor for determining a flow rate of the portion of gas without the water, and a controller operably connected to the first flow sensor and to the second flow sensor for determining the moisture content of the gas.

In a fourth aspect, a method for measuring moisture of gas includes determining a first flow rate of a portion of the flow of the gas, removing water from the portion of the flow of gas, and determining a second flow rate of the portion of the flow of the gas without the water.

BRIEF DESCRIPTION OF THE DRAWINGS

The subject matter which is regarded as the invention is particularly pointed out and distinctly claimed in the concluding portion of the specification. The invention, however, together with further objects and advantages thereof, may best be understood by reference to the following detailed description of the preferred embodiments and the accompanying drawings in which:

DETAILED DESCRIPTION

Figure 1:
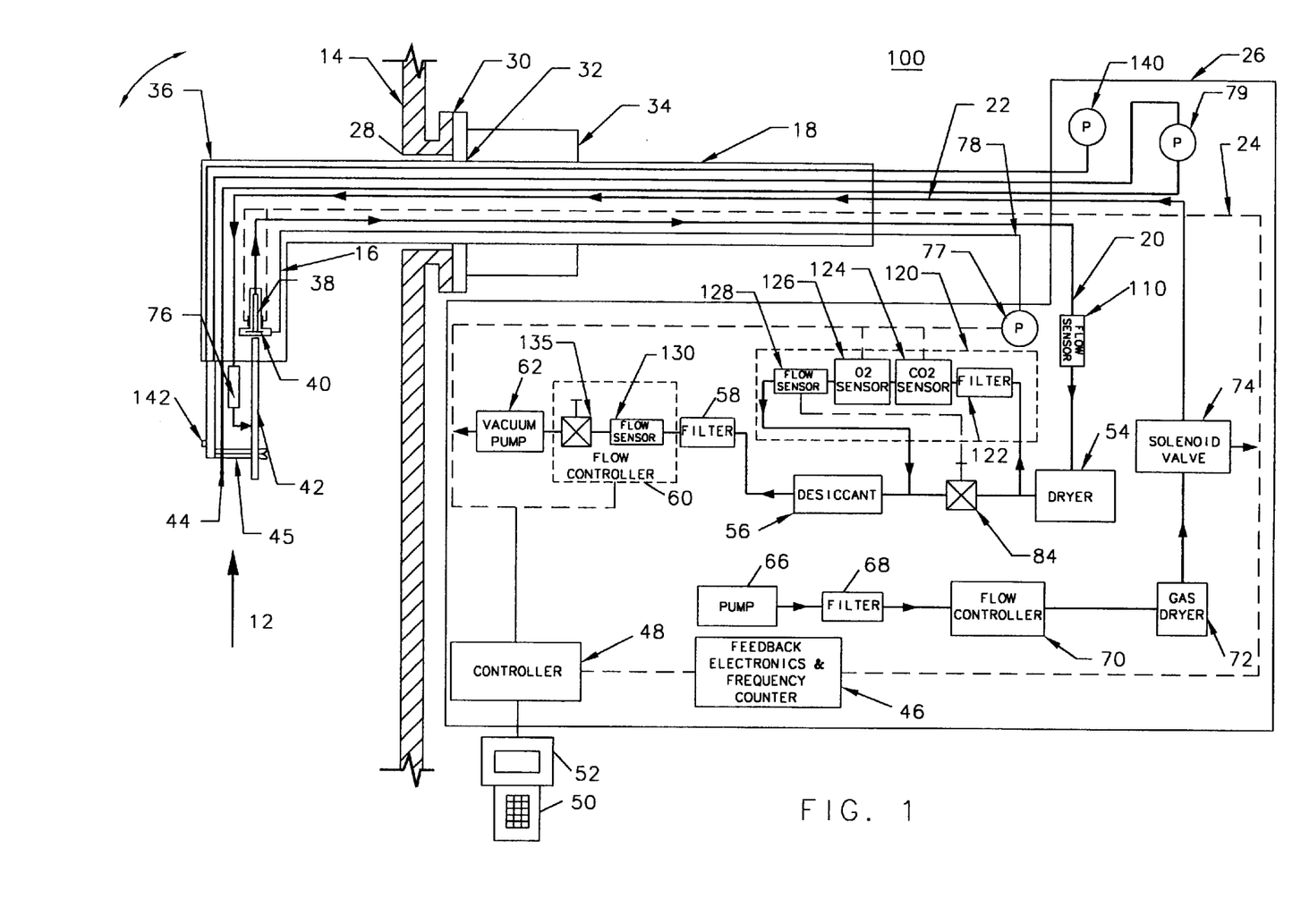
FIG. 1 is a schematic representation of one embodiment of the present invention for a particulate mass measurement instrument operable to measure moisture content of effluent gas in real-time for real-time adjustment of isokinetic sampling during measurement of the mass of particulate in the effluent gas.

FIG. 1 illustrates a particulate mass measurement instrument 100 for measuring the mass of particulate in an effluent gas 12 flowing within a stack 14 in accordance with the present invention. As explained in greater detail below, particulate mass measurement instrument 100 incorporates a monitor or means for measuring the moisture content of effluent gas 12 in real-time and real-time adjustment of isokinetic sampling based on the real-time measurement of the moisture content of the effluent gas during measurement of the mass of particulate in effluent gas 12. As used herein, the term "real-time" means substantially the actual time during which the sampling takes place.

Particulate mass measurement instrument 100 is similar, and includes improvements as explained in greater detail below, to the particulate mass measurement instrument described in U.S. Pat. No. 5,970,781 issued to Hiss, III, et al., entitled "In-Stack Direct Particulate Mass Measurement Apparatus and Method", and U.S. Pat. No. 6,016,688 issued to Hiss, III, et al., entitled "In-Stack Direct Particulate Mass Measurement Apparatus and Method with Pressure/Flow Compensation." The subject matters of these patents are incorporated in their entirety herein by reference.

For example, mass measurement instrument 100 includes a mass measurement assembly or probe 16 supported within stack 14 at the end of an extendible boom 18, or other support structure. Mass measurement assembly 16 is connected via pneumatic lines 20 and 22 and electrical signal line 24 to a control unit 26. The pneumatic and electrical signal lines preferably extend along and through boom 18. Advantageously, pneumatic lines 20 and 22 can be controllably heated, in whole or part. Control unit 26 may be located proximate boom 18 or remote therefrom.

The term "stack" is broadly used herein to connote any passageway that has particulate laden gas flowing through it. The term "effluent gas" is used herein to denote any such particulate laden gas. The invention is applicable to any facility which emits particulate laden gas. Such facilities are sometimes referred to in this industry as "stationary sources" and include, but are not limited to: coal burning facilities, garbage incinerators, hazardous waste type incinerators, cement plants, paper/pulp processing facilities, boiler exhaust, and smoke stacks.

As shown in FIG. 1, the wall of stack 14 might typically include a port 28 defined by an exterior flange 30. According to one embodiment of the present invention, a sliding joint 32 and bearing housing 34 are mounted to an outside surface of flange 30. Port 28, sliding joint 32 and bearing housing 34 define an interior passageway through which mass measurement assembly 16 and boom 18 can be inserted into stack 14. Mass measurement assembly 16 and boom 18 have an outer diameter slightly smaller than that of port 28. Mass measurement assembly 16 is mounted to the end of boom 18 by a rotating joint or pivot 36. This joint allows mass measurement assembly 16 to be-oriented coaxially with boom 18 for access into stack 14 through port 28. Following insertion, mass measurement assembly 16 is rotated about joint 36 to an orientation, as shown in FIG. 1, which facilitates sampling of effluent gas 12. After sampling is completed, mass measurement assembly 16 can be rotated back to its coaxial orientation with boom 18 for ready withdrawal from stack 14 through port 28. Various conventional mechanisms can be used to provide the rotational support and movement to mass measurement assembly 16, as will be appreciated by those skilled in this art.

While port 28 provides access to the interior of stack 14, sliding joint 32 and bearing housing 34 allow. boom 18 and attached mass measurement assembly 16 to be displaced in order to traverse the interior of the stack, as may be required or desired under various measurement protocols. A quick release clamp (not shown) may be used to temporarily lock slidable boom 18 in place when mass measurement assembly 16 is positioned at a desired crosswise location within stack 14. Boom 18 is preferably extendible to a maximum desired traverse length, and collapsible to adapt to various field conditions and for ease of transport.

Mass measurement assembly 16 includes a mass transducer 38 connected to a particulate collector 40, and an inlet tube 42 for directing sampled effluent gas 12 towards collector 40. Although the components of mass measurement assembly 16 may take many different forms, mass transducer 38 is preferably an inertial mass measurement transducer which provides a direct, real-time measure of the mass of particulate collected on collector 40. Mass transducer 38 can advantageously take the form of a hollow elastic element oscillating in a clamp-free mode, as more fully described hereinafter. Collector 40 preferably comprises a filter mounted to mass transducer 38. An impaction plate or other particulate matter collector can also be used to collect particulate from the sampled effluent gas. Inlet tube 42 is preferably short and straight to minimize inlet losses.

Mass measurement assembly 16 can be used to measure total particulate mass levels, or in conjunction with a cyclone or other device (not shown) that separates particles based on aerodynamic diameter, located upstream of inlet tube 42, to measure, for example, $PM_{10}$ or $PM_{2.5}$ particulate mass levels as is well known in the art.

Collector 40 is preferably located near the exit of inlet tube 42 in order to minimize transport losses and ensure integrity of the sample. Collector 40 preferably comprises an exchangeable filter cartridge mounted on the free end of the preferred transducer a hollow elastic element which is made to oscillate in a clamp-free mode. Construction and operation of an inertial mass measurement instrument employing such an oscillating hollow elastic element is described in detail in commonly assigned U.S. Pat. Nos. 3,926,271 and 4,391,338, and in a Japanese patent publication JP2-324364 (which patents and Japanese patent publication are incorporated in their entirety herein by reference).

For example, the mass transducer 38 is preferably a hollow tube, clamped at one end and free to vibrate at the other. An exchangeable filter cartridge is placed over the tip of the free end. This cantilevered elastic element vibrates at precisely its natural frequency. An electronic control circuit 46 senses its vibration and, through positive feedback, adds sufficient energy to the system to overcome losses. An automatic control circuit (not shown) maintains the vibration during measurement. A precise electronic counter 46 measures the frequency, which has a direct relationship with mass.

Tracking frequency with time yields the mass rate, and when combined with measured flow rate through the filter, produces the mass concentration. Such tracking and calculations can be readily accomplished, in known fashion by a computer/controller or processor 48 in control unit 26. A keypad 50 and display 52, or other input/output devices can be connected to controller 48 to facilitate operator interface therewith and to indicate mass readings provided by mass measurement instrument 100. U.S. Pat. No. 5,970,781 further describes the technique for mass measurement using a mass transducer, as well as a process for in-situ calibration of the mass transducer. U.S. Pat. No. 6,016,688 also describes pressure/flow compensation using a pressure transducer 77.

Referring again to FIG. 1, sampling line 20 connects mass transducer 38, e.g. the described hollow elastic element, to a dryer 54 such as, for example, a condenser, located outside of stack 14. At least a portion of sampling line 20 is preferably heated to prevent moisture condensation therein. Dryer 54 in conjunction with optional desiccant 56 serve to remove moisture and thoroughly dry the sampled gas before it passes through an additional optional filter 58, flow controller 60 and is exhausted through reduced pressure (e.g. vacuum) pump 62. Dryer 54 may be a condenser, a membrane type dryer or any other device or combination of devices that will dry a gas stream, preferably without affecting its $O_2$ or $CO_2$ content.

In operation, effluent gas 12 enters inlet tube 42 and passes directly therethrough to collector 40 mounted on the oscillating element or other mass transducer 38. The particulate matter in the sampled effluent gas can be collected by collector 40 at stack temperature as described in EPA Method 17. The sampled gas then proceeds through heated sampling line 20 in boom 18 to dryer 54 and then through the remaining elements of the sampling train. In this manner, direct measurements of the mass of particulate matter deposited on collector 40 can be obtained in real-time on-site.

EPA Method 17 requires the removal of uncombined water from a collected sample. As more fully described in U.S. Pat. No. 6,016,688, mass measurement instrument 100 provides for in-stack purging of such uncombined water, as well as equilibration of the collector prior to and after sampling. Equilibration comprises establishing a stable, reproducible thermodynamic condition for the collector before and/or after sampling. Collector conditioning between intermittent sampling periods can also be effectuated.

Accordingly, line 22 may be a conditioned gas line which extends through boom 18 and connects to inlet tube 42 in order to selectively supply conditioned gas to collector 40. The conditioned gas preferably comprises a dry clean gas provided by a pump 66 through a filter 68, a flow controller 70, a gas dryer 72, and a solenoid valve 74 to line 22. The components of this conditioned gas train may be conventional, off-the-shelf type elements. Such elements are preferably located in control unit 26 outside of stack 14.

Also associated with the conditioned gas line is a heat exchanger 76 or other conditioned gas temperature controller. As shown in FIG. 1, heat exchanger 76 is preferably located within stack 14 to conveniently ensure that the conditioned gas stream is at the effluent gas temperature. The heat exchanger may be either active, passive or a combination of both active and passive. Temperature sensor 44 can be employed for such active control. The heat exchanger may take various known forms. A section of the conditioned gas line upstream of heat exchanger 76 can optionally be heated to preheat the gas entering the exchanger. If desired, heat exchanger 76 or other temperature controller can be used to adjust the temperature of the conditioned gas to any set temperature, e.g. a temperature higher than that of the effluent gas.

Flow controller 70 controls the rate of flow of the conditioned gas while filter 68 and gas dryer 72 serve to ensure that the conditioned gas is clean and dry. Solenoid valve 74 serves to quickly turn on and off the supply of conditioned gas to line 22. When not in use, the conditioned gas is exhausted through solenoid valve 74. The activation and operation of the components of the conditioning gas train, as well as the components of the sampling train can all be controlled by controller 48, in known fashion.

The conditioned gas can advantageously be provided with a flow rate greater than that of the sampled effluent gas so that when collector 40 is to be conditioned, equilibrated, pressure/flow calibrated and/or purged by the conditioned gas, effluent gas is prevented from reaching the collector, i.e. backflow of the conditioned gas towards the entrance of inlet tube 42 due to its higher flow rate effectively blocks the entry of effluent gas into tube 42.

Alternatively, the flow along sampling line 20 can be controlled to effectively dilute the sampled effluent gas with conditioned gas. This approach might be used to extend collector life or to reduce the amount of moisture reaching the collector in order to enhance the ability of the collector to collect particulate or to decrease any postconditioning time.

When the flow rate of the conditioned gas is such as to prevent effluent gas sampling, the conditioned gas can be employed to equilibrate collector 40 in situ. Such equilibration can be used to precondition the collector prior to sampling and to postcondition the collector and any collected particulate after sampling, yielding results directly comparable to EPA Method 17, while avoiding the difficulties and delays associated with laboratory equilibration. Such collector conditioning can also be effectuated between intermittent sampling periods thereby extending the available life of the collector.

The conditioned gas line can provide for a constant stable flow rate to and a constant temperature at the collector during conditioning and sampling. In situ conditioning thus does not disturb the state of the collector-mass transducer combination.

Particulate mass measurement instrument 100 of FIG. 1 may be operated in various modes: continuous measurements at a single point, timed traverse measurements at multiple points, or time proportioned (intermittent) sampling, e.g. for calibration of indirect continuous emission monitors. Continuous uninterrupted sampling is used for relatively short duration tests, on the order of a few hours, similar to an EPA Method 17. Because collector life is a function of the type of particulate matter as well as the concentration, test durations on the order of days may be possible.

Collector life can be extended by sampling for only a portion of the time. This "time proportioned sampling" technique lengthens the time between collector changes, and can be used to calibrate present continuous monitors on a regular basis. For example, a scheme where sampling by instrument 100 occurs for a short time each hour and is compared with opacity readings taken by a separate continuous emission monitor during the same period would allow the constant updating of the continuous monitor calibration.

A typical sequence of operation for the particulate mass measurement instrument 100 will now be described. Initially the complete instrument is checked for leaks and then collector 40 is installed in mass measurement assembly 16. Mass measurement assembly 16 coaxially aligned at the end of boom 18 is then inserted through access port 28 into stack 14 and rotated into its sampling position with conditioned gas line 22 activated. The flow rate of the conditioned gas into inlet tube 42 prevents any effluent gas 12 from reaching collector 40 and permits preconditioning of this collector within the stack. The instrument is allowed to stabilize, i.e. the temperature of the conditioned gas, due to the heat exchanger or other temperature controller, rises to that of the effluent gas. This preconditioning establishes a zero baseline for future mass readings.

Once collector 40 has been preconditioned, sampling can begin by activating solenoid valve 74 to shut off the supply of conditioned gas to collector 40. Sampling line 20 now draws effluent gas in through inlet tube 42 for collection of particulate matter on collector 40.

The present invention is directed to further improvements of the above described particulate mass measuring instrument. In particular, mass measurement instrument 100 includes a moisture monitor or means for measuring the moisture content of the effluent gas in real-time which measured moisture content is used to determine the molecular weight of the effluent gas in real-time, and the velocity of the effluent gas 12 in real-time. Thus, as described below, determining the moisture content of the effluent gas enables real-time isokinetic sampling during measurement of the mass of particulate in effluent gas 12.

The means for measuring the moisture content of the effluent gas 12 is desirably incorporated into sampling line 20. For example, the means for measuring the moisture content in effluent gas 12 generally includes a first flow sensor 110, means 120 for measuring the molecular weight of the effluent gas without water (dry effluent gas) which is connected between dryer 54 and desiccant 56, and flow controller 60 having a second flow sensor 130. Means 120 for measuring dry effluent gas generally includes a filter 122, a carbon dioxide ($CO_2$) sensor 124, an oxygen ($O_2$) senor 126, and a third flow sensor 128, which are connected in series.

Although various types of flow sensors, e.g. mass or volumetric, may be used, preferred flow sensors are desirably orifice type flow meters which employ Bernoulli's Theorem in which the volumetric flow rate through an orifice is proportional to the square root of the pressure drop across the orifice and the fluid density. A suitable volumetric flow sensor is described in U.S. Pat. No. 5,792,966 issued to Weitz et al. entitled "Thermally Stable, Fluid Flow Measurement Device," the entire subject matter of which is incorporated herein by reference.

The volumetric flow rate of a gas flowing through the orifice of this sensor is determined from the following equation:

$$Q = m\left[\sqrt{\frac{\Delta P \times T}{P \times MW}}\right] + b \quad (2)$$

where:

Q=Volumetric flow rate $\Delta P$=Pressure drop across the orifice

T=Absolute temperature of the gas at the flow sensor

P=Absolute pressure of the gas at the inlet of the flow sensor m, b=Calibration constants MW=Molecular weight of the gas at the flow sensor As is known, mass flow rate can be calculated from the volumetric flow rate through multiplication by the density of the gas at the flow sensor.

$$\dot{m} = Q \times \rho \quad (3)$$

where:

$\dot{m}$=Mass flow rate

Q=Volumetric flow rate, and $\rho$=Density of gas at the flow sensor

Figure 2:
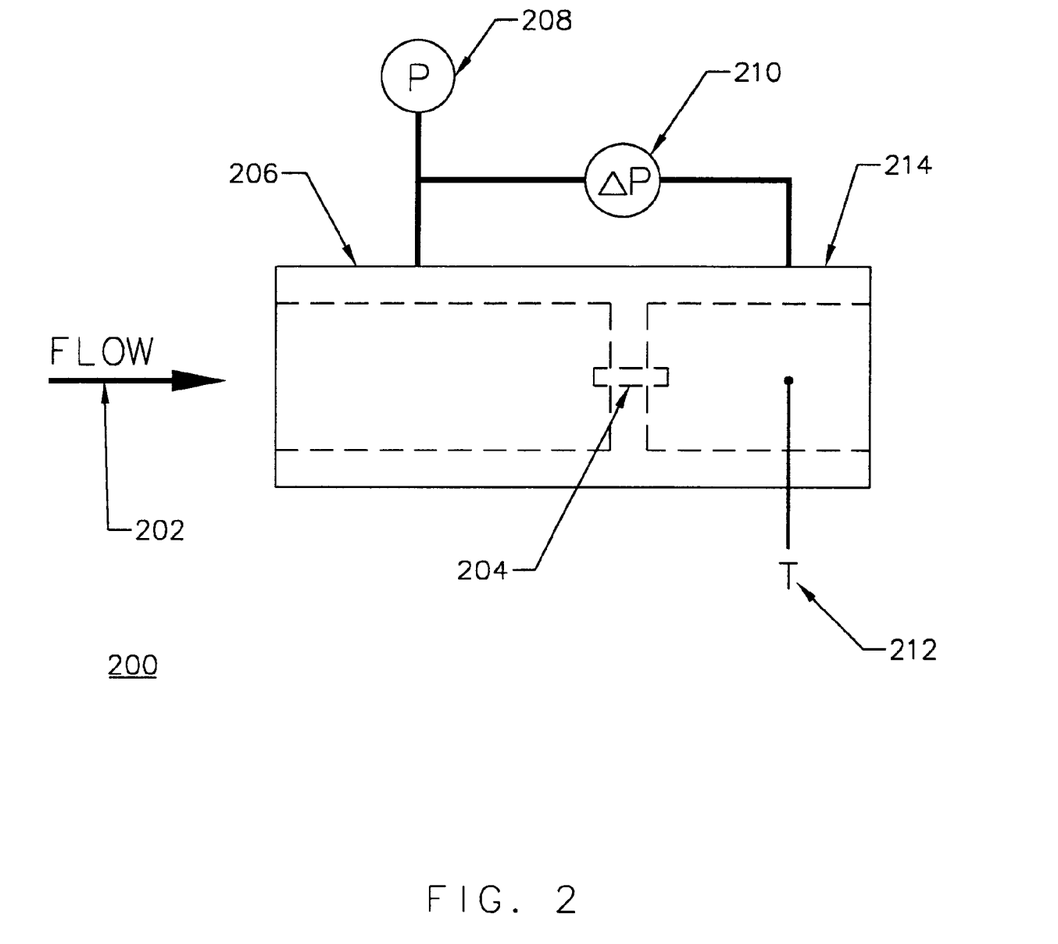
FIG. 2 is a schematic representation of a flow sensor suitable for use in the instrument of FIG. 1.

FIG. 2 schematically illustrates the presently preferred configuration of a flow sensor 200 for determining the flow rate of a gas 202. Sensor 200 includes an orifice 204 such as that described in U.S. Pat. No. 5,792,966. Pressure transducer 208 is used to determine the absolute pressure (P) in sensor inlet 206 while pressure transducer 210 determines the pressure drop ($\Delta P$) across orifice 204. A thermocouple 212 can be used to determine the absolute temperature (T) of the gas in the sensor. Sensor housing 214 may be made of any suitable material such as plastic when used for dry effluent gas flow sensors 128 and 130 (FIG. 1), but preferably comprises a high temperature tolerant and corrosion resistant material, such as stainless steel, when used in flow sensor 110 which receives the hot, moist effluent gas drawn from the stack.

The pressure and temperature readings from flow sensors 110, 128 and 130 are provided to controller 48 which calculates the flow rate of each sensor therefrom in accordance with the above presented equations. For these calculations, the molecular weight (MW) of the dry effluent gas passing through flow sensors 128 and 130 (hereinafter referred to as the dry molecular weight Md) can be derived from readings provided by carbon dioxide sensor 124 and oxygen sensor 126, as described hereinafter with reference to equation (5).

The wet molecular weight Ms for flow sensor 110 is calculated from the dry molecular weight Md and the quantity of water vapor contained in the moist effluent gas (as described hereinafter with regard to equation 4). The quantity of water vapor contained in the. gas is not exactly known but may be approximated for this purpose, by, for example, using a previous calculation of the proportion of water vapor by volume Bws (as described hereinafter with regard to equation 8) as the present proportion. A similar approach can be used for density calculations. All calculations are performed and all sensors are read every few seconds. During this short period, changes to the quantity of water vapor in the gas are sufficiently small resulting in negligible error.

According to the present invention, as explained in greater detail below, the pair of flow sensors 110 and 130 connected in series separated by dryer 54, allow comparison of the flow rate of the effluent gas with water vapor and the flow rate of the effluent gas without water to provide a real-time moisture measurement.

As described above, effluent gas velocity V is determined according to the following relationship:

$$V = C \times (PitotDP)^{0.5} \times (T/(P \times Ms))^{0.5} \quad (1)$$

where:

C is the pitot tube calibration constant;

PitotDP is the measured pressure drop across the pitot tube;

T is the absolute effluent gas temperature;

P is the absolute pressure of the effluent gas; and

Ms is the molecular weight of the effluent gas including water vapor.

To obtain in real time, T, the PitotDP, and P, instrument 100, may, for example, include a temperature sensor 44, a pitot tube 45, a pressure transducer 79 which determines the pressure drop across pitot tube 45, and a pressure transducer 140 which in conjunction with a static pressure tap 142 measures the static pressure of the stack. The absolute pressure P is equal to the current barometric pressure added to the measured static pressure of the stack.

As also discussed above, the measurement of the total molecular weight of the effluent gas requires measurement of the water vapor. The following method efficiently determines the moisture content in real-time allowing a determination of the measurement of the molecular weight of the effluent gas including the water vapor, Ms, in real-time. The molecular weight of the effluent gas, including water vapor, is then used to maintain true isokinetic sampling throughout a test particularly where source conditions may be constantly changing.

The measurement of wet molecular weight of the effluent gas can be broken into two components; the measurement of the dry molecular weight, Md, and the measurement of the moisture content of water vapor by volume, Bws, as follows:

$$Ms = ((1, -Bws) \times Md) + (MWwv \times Bws) \quad (4)$$

where:

MWwv=Molecular weight of water vapor (18.0153 lb/lb*mole).

The dry molecular weight, Md, is determined by gas sensors in real-time. For example, the dry molecular weight measurement is made by reading $CO_2$ sensor 124 and $O_2$ sensor 126 with the remainder of the gas composition assumed to be nitrogen ($N_2$). This assumption holds true for most combustion sources. The dry molecular weight, Md, is determined as follows:

$$Md = 0.28 \times [100 - (\%CO_2 + \% O_2)] + (0.32 \times \% O_2) + (0.44 \times \% CO_2) \quad (5)$$

where:

0.28=Molecular weight of nitrogen/100;

0.32=Molecular weight of oxygen/100; and 0.44=Molecular weight of carbon dioxide/100

Generally, the measurement of the volume fraction of water vapor, Bws, is determined by drawing a portion of the effluent gas through supply line 20 using pump 62, passing the portion of the effluent gas through first flow sensor 110, drying and passing the portion of the effluent gas through second flow sensor 130. The volume of water vapor in the gas stream at any instant is derived from the difference in flow rates determined by the flow sensors converted to a volumetric flow rate at stack conditions as more fully described hereinafter with respect to equations (6) and (7). The percent water vapor by volume, Bws, is the volumetric flow rate of water vapor compared to the total volumetric flow at stack conditions.

More specifically, a portion of the effluent gas is sampled (as described below isokinetically) and filtered at the mass transducer to remove particulate. It is then transported to first flow sensor 110 maintained at an elevated temperature ensuring all water remains a vapor. The effluent gas is then transported to dryer 454 removing all the water and thereby reducing the dew point to −20 degrees C. During the drying process the temperature is reduced to approximately ambient.

The portion of the effluent gas is then desirably split into parallel flows, one parallel leg transports effluent gas to gas sensors, $CO_2$ sensor 124 and $O_2$ sensor 126, for determining the dry molecular weight measurement Md. This leg is then recombined with the other leg. Splitting the flow allows the flow through $CO_2$ sensor 124 and $O_2$ sensor 126 to remain constant, which aids in obtaining an accurate measurement. The flow of effluent gas through $CO_2$ sensor 124 and $O_2$ sensor 126 is regulated by proportional valve 84 operably connected to flow sensor 128.

The dried effluent gas is then transported through desiccant 56, filter 58, and then to second flow sensor 130 which is in communication with a proportional valve 135 providing control of the sampling flow rate. The sampling flow rate is continuously adjusted to maintain isokinetic conditions at the sample inlet. The gas is then exhausted through vacuum pump 62.

The difference between a measured mass flow rate at first flow sensor 110 and a measured mass flow rate at second flow sensor 130 divided by the density of water vapor at stack conditions yields the volumetric flow rate, $Q_{wv}$, of the water vapor removed by the dryer, as follows:

$$Q_{wv} = \frac{\dot{m}_1 - \dot{m}_2}{\rho_{wv})_{T,Pstack}} \quad (6)$$

where:

$\dot{m}_1$=Mass flow rate (hot, moist effluent gas);

$\dot{m}_2$=Mass flow rate (dry, ambient effluent gas); and $\rho_{wv})_{T,Pstack}$=Density of water vapor at stack temperature and pressure Alternatively, the volumetric flow rate Qwv of the water vapor may be determined from volumetric flow rates of the first and second flow sensors, as follows:

$$Q_{wv} = \frac{Q_1 \times \rho_1}{\rho_{wv})_{T,Pstack}} - \frac{Q_2 \times \rho_2}{\rho_{wv_{T,Pstack}}} \quad (7)$$

where:.

$Q_1$=Volumetric flow rate at the first sensor;

$\rho_1$=Density of the effluent gas at the first sensor;

$Q_2$=Volumetric flow rate at the second sensor, $\rho_2$=Density of the effluent gas at the second sensor; and $\rho_{wv})_{T,Pstack}$=Density of water vapor at stack temperature and pressure.

A ratio of the volumetric flow rate of water vapor compared to the total volumetric flow rate at stack conditions yields the proportion of water vapor by volume, Bws, as follows:

$$B_{ws} = \frac{Q_{wv}}{Q_1 \times \frac{T_1}{P_1} \times \frac{P_{Stack}}{T_{Stack}}} \quad (8)$$

where:

$Q_{wv}$=Volumetric flow rate of water content in effluent gas;

$Q_1$=Volumetric flow rate of hot, moist effluent gas at the first flow sensor, $T_1$=Absolute temperature of hot, moist effluent gas at the first flow sensor;

$P_1$=Absolute pressure of hot, moist effluent gas at the first flow sensor;

$P_{Stack}$=Absolute pressure of effluent gas in the stack; and $T_{Stack}$=Absolute temperature of effluent gas in the stack Knowing the proportion of water vapor by volume, Bws, the molecular weight of the effluent gas, Ms, can be determined using Equation 4 in real-time, and thus the effluent gas velocity, V, using Equation 1 in real-time. The real-time determination of velocity can be used by controller 48 to control proportional valve 135 to vary the velocity of the sampled effluent gas. The isokinetic flow rate is adjusted in real-time based on the moisture content measurement to provide a "true" isokinetic sampling accounting for molecular weight fluctuations in the effluent gas.

At the conclusion of sampling, solenoid valve 74 is again activated to supply the conditioned gas to inlet tube 42. The higher flow rate of the conditioned gas again blocks effluent gas from reaching the collector. The dry, clean, heated conditioned gas removes uncombined water and serves to postcondition the collector and collected particulate.

Following the postconditioning, mass measurement assembly 16 is withdrawn from stack 14 through access hole 28, the conditioned gas line 22 is deactivated and mass measurement assembly 16 is preferably temperature stabilized outside stack 14, for example with an insulation blanket, to maintain mass measurement assembly 16 at substantially the stack temperature. With the sampling line 20 still activated, the interior of inlet tube 42 can then be brushed down several times to collect and measure, using the same measurement instrument 100, any particulate matter which may have lodged along the interior walls of the tube during sampling. The mass reading from brush down can be added to the mass reading obtained during sampling to provide a more accurate indication of the total mass particulate in the effluent gas.

The conditioned gas may also be advantageously used to condition the collector between time proportioned (i.e. intermittent) sampling periods. The difference in total mass readings between consecutive stabilized conditioning periods provides a measure of the mass increase occurring during the intermediate sampling period.

The accuracy of first flow sensor 110 and second flow sensor 130 can be improved by performing the following calibration. With second flow sensor 130 assumed to be accurate, it is used to calibrate and adjust first flow sensor 110. Real-time moisture measurement requires the difference between the flow sensors be calculated, and in the case where dry gas is flowing through the system, the difference must be sufficiently close to zero.

The calibration procedure consists of comparing the flow rates measured by flow sensors 110 and 130 at, for example, four flow rates. A linear regression on the data yields the adjustment necessary for accurate moisture measurement. The linear regression can be used to adjust flow sensor 110 according to the following equation.

$$\dot{m}_1 = M \times \dot{m}_2 + b \quad (9)$$

where:

$\dot{m}_1$=Mass flow rate measured by flow sensor 110;

$\dot{m}_2$=Mass flow rate measured by flow sensor 130;

M=Slope result of linear regression; and b=Y—intercept result of linear regression The procedure involves:

1. Varying the flow rate using flow controller 60;
2. Plotting values of $\dot{m}_1$ verses $\dot{m}_2$ at each discrete flow; and
3. Determining a linear regression of the data to yield M and b correction to mass flow sensor 110.

$\dot{m}_1$ are $\dot{m}_2$ mass flow rates at standardized condition (temperature and pressure) which is used when comparing the mass flow rates of the flow sensors to determine the removal of a constituent such as water.

From the present description, it will be appreciated by those skilled-in the art that the moisture monitor of the present invention may be configured as a stand alone unit, i.e., not incorporated or integrated into the mass measurement assembly or instrument. For example, a stand alone moisture monitor according to the present invention may be used in combination with measurement assemblies or instruments such as stand alone inertial mass measurement instruments, or with continuous emission monitors used for measuring various regulated pollutants, or in other applications.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the following claims.

What is claimed is:

1. A particulate mass measurement apparatus for measuring mass of particulate of effluent gas flowing in a stack, said apparatus comprising:

a mass measurement assembly for measuring the mass of particulate of the effluent gas flowing in the stack;

means for measuring in real-time moisture content of the effluent gas flowing in the stack, said means for measuring moisture content comprising a first flow sensor for determining a first flow rate of a portion of a flow of the effluent gas, a dryer for removing water from the portion of the flow of effluent gas, and a second flow sensor for determining a second flow rate of the portion of the flow of the effluent gas without the water;

a controller for controlling isokinetic sampling of the effluent gas measurable by said mass measurement assembly based on real-time moisture content of the effluent gas flowing in the stack; and a pressure transducer and a temperature sensor for determining absolute pressure and absolute temperature, respectively, at the first flow sensor.

2. The particulate mass measurement apparatus of claim 1 wherein said controller is operable to control isokinetic sampling in real-time.

3. The particulate mass measurement apparatus of claim 1 wherein said mass measurement assembly provides measurement of the mass of particulate in real-time.

4. The particulate mass measurement apparatus of claim 1 wherein said first flow sensor and said second flow sensor each comprise a volumetric flow sensor.

5. The particulate mass measurement apparatus of claim 1 wherein said means for measuring moisture content further comprises a carbon dioxide sensor and an oxygen sensor for use in measuring molecular weight of the effluent gas.

6. The particulate mass measurement apparatus of claim 1 wherein said controller determines a velocity V of the effluent gas for isokinetic sampling in accordance with the following formula:

$$V = C \times (PitotDP)^{0.5} \times (T/(P \times Ms))^{0.5}$$

where:

C represents a pitot tube calibration constant;

PitotDP represents a measured pressure drop across a pitot tube in the effluent gas;

T represents an absolute effluent gas temperature;

P represents an absolute pressure of the effluent gas; and

Ms represents a molecular weight of the effluent gas including water vapor.

7. The particulate mass measurement apparatus of claim 6 wherein a measurement of said molecular weight of the effluent gas, Ms, is determined in accordance with the following formula:

$$Ms=((1-Bws) \times Md)+(MWwv \times Bws)$$

where:

MWwv represents a molecular weight of water vapor;

Md represents a dry molecular weight of the effluent gas; and

Bws represents a proportion of water vapor by volume.

8. The particulate mass measurement apparatus of claim 7 wherein said proportion of water vapor by volume Bws is determined in accordance with the following formula:

$$B_{ws} = \frac{Q_{wv}}{Q_1 \times \frac{T_1}{P_1} \times \frac{P_{Stack}}{T_{Stack}}}$$

where $Q_{wv}$=Volumetric flow rate of water content in effluent gas;

$Q_1$=Volumetric flow rate of hot, moist effluent gas at a first flow sensor;

$T_1$=Absolute temperature of hot, moist effluent gas at the first flow sensor as determined by the temperature sensor;

$P_1$=Absolute pressure of hot, moist effluent gas at the first flow sensor as determined by the pressure transducer;

$P_{Stack}$=Absolute pressure of effluent gas in the stack; and $T_{Stack}$=Absolute temperature of effluent gas in the stack.

9. The particulate mass measurement apparatus of claim 1 wherein said mass measurement assembly comprises a mass transducer, a particulate collector connected to said mass transducer, and an inlet tube for directing sampled gas toward said collector.

10. The particulate mass measurement apparatus of claim 1 further comprising a conditioned gas supply line for selectively supplying conditioned gas to said mass measurement assembly.

11. The particulate mass measurement apparatus of claim 10 wherein said conditioned gas supply line includes a pump, a flow controller, a dryer, and a switching valve.

12. A method for measuring mass of particulate of effluent gas flowing in a stack, the method comprising:

determining a moisture content measurement of the effluent gas in real time;

obtaining an isokinetic sample of a portion of the effluent gas based on real-time moisture content measurement of the effluent gas, including a step of determining a proportion of water vapor by volume Bws of the effluent gas in accordance with the following formula:

$$B_{ws} = \frac{Q_{wv}}{Q_1 \times \frac{T_1}{P_1} \times \frac{P_{Stack}}{T_{Stack}}}$$

where:

$Q_{wv}$=Volumetric flow rate of water content in effluent gas;

$Q_1$=Volumetric flow rate of hot, moist effluent gas at a first flow sensor;

$T_1$=Absolute temperature of hot, moist effluent gas at the first flow sensor as determined by a temperature sensor;

$P_1$=Absolute pressure of hot, moist effluent gas at the first flow sensor as determined by a pressure transducer;

$P_{Stack}$=Absolute pressure of effluent gas in the stack; and $T_{Stack}$=Absolute temperature of effluent gas in the stack; and obtaining a measurement of mass of particulate of the isokinetic sample.

13. The method of claim 12 wherein the obtaining the isokinetic sample is in real-time.

14. The method of claim 13 wherein the obtaining the measurement of mass of particulate of the isokinetic sample is in real-time.

15. The method of claim 12 wherein the obtaining the isokinetic sample comprises determining a molecular weight of the effluent gas.

16. The method of claim 12 wherein the obtaining the isokinetic sample comprises determining a velocity of the effluent gas.

17. The method of claim 12 wherein the obtaining the isokinetic sample comprises determining a molecular weight of the effluent gas without water.

18. The method of claim 17 wherein the determining the molecular weight of the effluent gas without water comprises measuring the concentration of carbon dioxide and oxygen of the effluent gas.

19. The method of claim 12 wherein the determining the moisture content measurement comprises determining a first flow rate of a portion of a flow of the effluent gas, removing water from the portion of the flow of effluent gas via a dryer, and determining a second flow rate of the portion of the flow of the effluent gas without the water.

20. The method of claim 19 wherein determining the moisture content measurement further comprises determining a difference between said first flow rate and said second flow rate.

21. The method of claim 12 wherein obtaining an isokinetic sample comprises determining a velocity V of the effluent gas according to the following relationship:

$$V=C \times (PitotDP)^{0.5} \times (T/(P \times Ms))^{0.5}$$

where:

C represents a pitot tube calibration constant;

PitotDP represents a measured pressure drop across a pitot tube in the effluent gas;

T represents an absolute effluent gas temperature;

P represents an absolute pressure of the effluent gas; and

Ms represents a molecular weight of the effluent gas including water vapor.

22. The method of claim 21 wherein the measurement of the molecular weight of the effluent gas, Ms, is determined in accordance with the following formula:

$$Ms=((1-Bws) \times Md)+(MWwv \times Bws)$$

where:

MWwv represents a molecular weight of water vapor;

Md represents a dry molecular weight of the effluent gas; and

Bws represents a proportion of water vapor by volume.

23. The method of claim 12 wherein the volumetric flow rate of water content in effluent gas Qwv is determined by calculating a difference between a flow rate of hot, moist effluent gas and a flow rate of said gas after water removal.

24. The method of claim 23 further comprising providing a conditioned gas to the mass measurement assembly.

* * * * *

UNITED STATES PATENT AND TRADEMARK OFFICE
CERTIFICATE OF CORRECTION

PATENT NO.    : 6,439,027 B1
DATED         : August 27, 2002
INVENTOR(S)   : Hiss, III It is certified that error appears in the above-identified patent and that said Letters Patent is hereby corrected as shown below:

Column 12,
Line 55, insert the word -- dry -- after the word "measuring"

Signed and Sealed this

Eighteenth Day of February, 2003

JAMES E. ROGAN
*Director of the United States Patent and Trademark Office*